United States Patent [19]
Pernick

[11] Patent Number: 5,735,145
[45] Date of Patent: Apr. 7, 1998

[54] WEFT KNIT WICKING FABRIC AND METHOD OF MAKING SAME

[75] Inventor: Bruce M. Pernick, Stamford, Conn.

[73] Assignee: Monarch Knitting Machinery Corporation, Glendale, N.Y.

[21] Appl. No.: 650,609

[22] Filed: May 20, 1996

[51] Int. Cl.⁶ ........................................ D04B 1/00
[52] U.S. Cl. ........................ 66/196; 66/193; 66/195; 66/197; 66/202; 604/378
[58] Field of Search ................ 66/193, 195, 197, 66/202; 604/378

[56] References Cited

U.S. PATENT DOCUMENTS

| | | | |
|---|---|---|---|
| 2,166,166 | 7/1939 | Larkin | 66/170 |
| 2,372,497 | 3/1945 | Johnson et al. | 66/190 |
| 2,879,654 | 3/1959 | Evans | 66/176 |
| 2,921,457 | 1/1960 | Evans | 66/176 |
| 4,079,602 | 3/1978 | Blore | 66/196 |
| 4,341,096 | 7/1982 | Safrit et al. | 66/185 |
| 4,378,683 | 4/1983 | Matsuda et al. | 66/193 |
| 4,399,671 | 8/1983 | Henningsson | 66/196 |
| 4,467,626 | 8/1984 | Coble et al. | 66/196 |
| 4,601,940 | 7/1986 | Fisher | 66/195 X |
| 4,678,693 | 7/1987 | Kemp | 428/91 |
| 4,733,546 | 3/1988 | Toda | 66/195 X |
| 4,785,558 | 11/1988 | Shiomura | 36/114 |
| 4,797,311 | 1/1989 | Kemp | 428/92 |
| 5,065,600 | 11/1991 | Byles | 66/193 |
| 5,095,548 | 3/1992 | Chesebro, Jr. | 2/239 |
| 5,141,794 | 8/1992 | Arroyo | 604/378 X |
| 5,284,031 | 2/1994 | Stoll et al. | 66/64 |
| 5,319,807 | 6/1994 | Brier | 2/239 |
| 5,373,713 | 12/1994 | Miller | 66/196 |
| 5,385,036 | 1/1995 | Spillane et al. | 68/87 |
| 5,395,684 | 3/1995 | Robinson et al. | 428/253 |
| 5,422,153 | 6/1995 | Miyamoto | 428/95 |
| 5,461,884 | 10/1995 | Depoe et al. | 66/195 X |
| 5,461,885 | 10/1995 | Yokoyama et al. | 66/170 |
| 5,528,910 | 6/1996 | Azais | 66/197 |
| 5,560,227 | 10/1996 | Depoe et al. | 66/195 X |

FOREIGN PATENT DOCUMENTS 43 36 303   4/1995   Germany.

*Primary Examiner*—John J. Calvert
*Attorney, Agent, or Firm*—Bell Seltzer Intellectual Property Law Group of Alston & Bird, LLP

[57] ABSTRACT

A multi-layer weft knit fabric for absorbing moisture and wicking it from a first fabric layer to a second layer is described, as well as a method for making the fabric. The multi-layer fabric includes a first hydrophobic layer and a second hydrophilic layer, with the layers being secured together by a series of courses forming spacer yarns which maintain the fabric layers in a spaced relationship relative to each other. The spacer yarns are adapted to wick moisture from the hydrophobic layer to the hydrophilic layer. The spacer yarns are preferably knit-in or laid-in to the respective knit fabric layers, and a plastic water-resistant layer can be secured proximate the hydrophilic fabric layer. A method of integrally knitting the multi-layer fabric on a circular knitting machine is also described.

31 Claims, 2 Drawing Sheets

WEFT KNIT WICKING FABRIC AND METHOD OF MAKING SAME

BACKGROUND OF THE INVENTION

1. Field of the Invention

The invention generally relates to a weft knit fabric for absorbing moisture and wicking it away from the fabric surface and a method for making the fabric. More specifically, the invention relates to a weft knit fabric having first and second parallel knit fabric layers, one of said layers being hydrophobic and the other layer being hydrophilic, said layers being joined together by a series of knit courses forming spacer yarns which secure the fabric layers together in a spaced relationship to each other and which wick moisture from the hydrophobic layer to the hydrophilic layer, and a method for knitting the same on a weft knitting machine.

2. Description of the Prior Art

Incontinent individuals, such as many elderly people and young children, historically have had difficulty in obtaining bedding materials specially suited for their specific needs. Mattresses for bedding are usually covered with cotton or cotton blend fabrics, which do not provide the mattresses with protection from moisture. The filling materials of mattresses, which tend to be absorptive, typically will rapidly soak up any type of liquid with which they come in contact. Obviously then, it is desirable to keep the mattresses from coming into contact with moisture or liquids. This can represent a significant problem for incontinent individuals, as a single accident can damage or even ruin an unprotected mattress. As a result, it is customary to cover a mattress with a plastic sheet, then cover the plastic sheet with a conventional fabric sheet such as one made from cotton, a cotton blend, satin or the like.

Even though the plastic sheet material is covered by regular sheet material, it tends to make a "crackling" noise when the bed user moves and tends to feel stiff to the bed user, thereby decreasing the bed comfort. In addition, when the plastic material folds or gathers in spots as a result of the weight of the wearer on the bed, protrusions can be formed which can project uncomfortably into the bed user's skin. This is a particular problem for those who are immobilized such as bedridden persons who cannot readily shift position in response to encountering such an uncomfortable protrusion.

Further, such plastic sheets can be difficult to clean and particularly to dry following washing, as many plastic sheeting materials do not tend to dry successfully in automatic dryers due to the high heats generally associated therewith. In addition, this layered sheet arrangement tends to provide unsatisfactory results because the combination of the sheet, whether absorbent or not, on top of the plastic sheet tends to maintain liquids on the surface of the arrangement. As a result, any such moisture is maintained proximate the bed user, causing discomfort and potential skin irritation or the like. Because separate cleaning processes are typically required for the plastic and regular sheets, maintenance of such can tend to be costly.

Commercially available bed pads adapted for use by incontinent individuals have failed to overcome the deficiencies associated with the plastic sheet and regular fabric sheet combinations. For example, one commercially available bed pad has a first layer of 100% cotton flannel and a second layer of moisture repellent polyester nylon. The two layers are sewn together about their respective peripheries and a row of zigzag stitches spaced inwardly from the edges of the periphery also joins the layers. As was the case with the plastic sheet in combination with the regular fabric sheet, this combination of an absorbent fabric on top of a plasticized material tends to keep the moisture proximate the surface of the bed pad and thus in contact with the bed user. Further, because of the stitches, the integrity of the water repellent layer is breached and moisture can seep through to the mattress. Thus, this type of bed pad fails to provide a comfortable waterproof barrier for mattresses.

Developments in materials capable of absorbing moisture and transporting it away from a wearer-contacting surface have generally been directed to garments for incontinent individuals in the form of disposable diapers. Such articles typically include an outer layer of plastic to which are secured multiple layers of absorbent material, which are usually pulp-based. An upper wearer-contacting layer generally has a moisture flow-through layer, which allows the passage-through of moisture to the absorbent layers. The numerous layers customarily included in such articles tend to make them relatively expensive. Thus, the manufacture of larger-sized items such as bedding articles or the like from these materials would likely be cost prohibitive. Because the materials used to make such articles do not tend to wash well, the items are characteristically disposable rather than being reusable. Therefore, the expense which would be present with a large article from such materials could not be rationalized on the basis of many uses of the item. Further, these products represent disposal problems; many experts have expressed concern over the rapid filling up of landfills due in large part to the widespread usage of these types of disposable diapers. This problem would be exacerbated even further by the introduction of large size articles from these materials such as bedding items and the like.

The fabric of the present invention comprises an integrally formed, weft knit fabric structure having first and second knit fabric layers which are secured in spaced relation to each other by a series of spacer yarns extending between the fabric layers.

Integrally formed, multiple layer knit fabrics per se are known, as illustrated, for example, by U.S. Pat. Nos. 5,284,031, 5,422,153, 5,395,684, and 4,785,558, to Stoll et al., Miyamoto, Robinson et al., and Shiomura, respectively. The patent to Stoll et al. describes a multiple layer knitted structure which can be produced on a two-bed, flat-bar knitting machine, and which is knit to include stable fabric webs connecting first and second parallel fabric webs. The patent to Miyamoto describes a weft knit composite fabric for decorating the interior and exterior of buildings, cars, furniture, bags or the like. The fabric has first and second knitted layers which are tied together by alternating courses of laid-in S- and Z-twist yarns.

The patent to Robinson et al. describes a double-faced knitted glass fiber fabric, in which the faces are interconnected by at least one linking thread which passes from one face to the other. The linking thread is described as preferably being made of glass fiber. The patent to Shiomura describes a warp knit shoe upper having an outer knit fabric layer, an inner knit layer, and a crossing thread which is "interknitted" to be bound into the outer and inner knit fabric layers. The wearer-contacting layer is described as desirably being made from natural, moisture absorptive yarn and the outer layer is desirably made from a synthetic yarn. There is no description of any wicking being performed, nor would any desirably be performed, since such would serve to wick moisture to the interior of the shoe, proximate the wearer's foot.

SUMMARY OF THE INVENTION

The present invention utilizes an integrally-formed weft knit fabric structure having a first knit fabric layer formed from hydrophobic yarns, a second knit fabric layer formed from hydrophilic yarns, and a plurality of spacer yarns integrally formed with the first and second fabric layers to secure those layers together in spaced relation to each other. For purposes of this invention, hydrophilic yarns and fabrics are those having a tendency to attract and hold onto moisture while hydrophobic yarns and fabrics are those not having such a tendency. The spacer yarns are adapted to wick moisture from the first hydrophobic layer to the hydrophilic layer. In this way, when an item such as an incontinence sheet is formed from the fabric, the hydrophobic sheet is adapted to lie adjacent the user so that moisture transport occurs in a direction away from the sheeting user. The spacer yarns are desirably sufficiently rigid to maintain the first fabric layer in a spaced orientation relative to the second fabric layer. In a preferred form of the invention, the hydrophilic layer is coated on its outer side (i.e. that more remote from the first layer) in order that the moisture transferred to the hydrophilic layer is maintained within that layer rather than being transferred to a mattress lying therebeneath.

In a preferred form of the invention, the fabric is knit on a circular knitting machine having both cylinder and dial needle beds. In this embodiment of the invention, one of the first and second layers is knit on the cylinder needles while the other fabric layer is knit on the dial needles, and the spacer yarns are alternately either knit or laid into the stitches of the first and second layers in alternating fashion, such that the spacer yarns traverse back and forth between the two layers. In a particularly preferred form of the invention, interlock gating is used for the two needle beds (i.e. the needles on the two beds are exactly opposite each other rather than offset as in conventional arrangements) and each needle bed includes alternating long and short needles in a manner known in the art with respect to interlock gating.

In a preferred form of the invention, the first substantially hydrophobic layer is knit from either spun, monofilament, or multifilament polyester yarns, while the hydrophilic layer is knit from yarns of cotton, rayon, or blends thereof. In a particularly preferred form of the invention, the substantially hydrophobic layer comprises a spun polyester yarn, the spacer yarns comprise non-textured polyester yarns, and the substantially hydrophilic layer comprises a cotton yarn.

DETAILED DESCRIPTION

The present invention will now be described more fully hereinafter with reference to the accompanying drawings, in which a preferred embodiment of the invention is shown. This invention may, however, be embodied in many different forms and should not be construed as limited to the embodiments set forth herein; rather, this embodiment is provided so that this disclosure will be thorough and complete and will fully convey the scope of the invention to those skilled in the art. Like numbers refer to like elements throughout.

Figure 1:
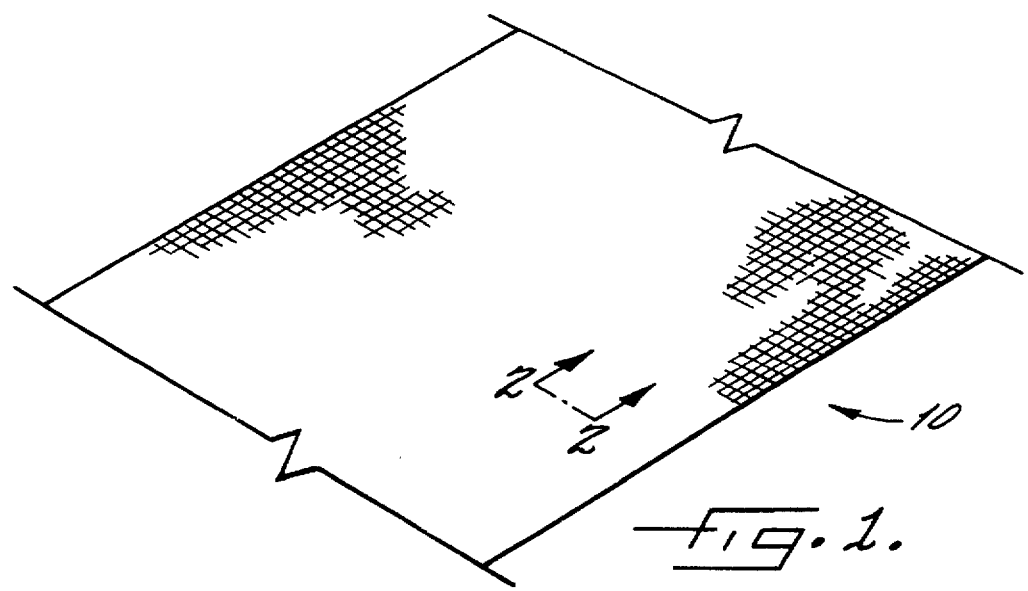
FIG. 1 is a perspective view of a piece of fabric made according to the present invention.
Figure 2:
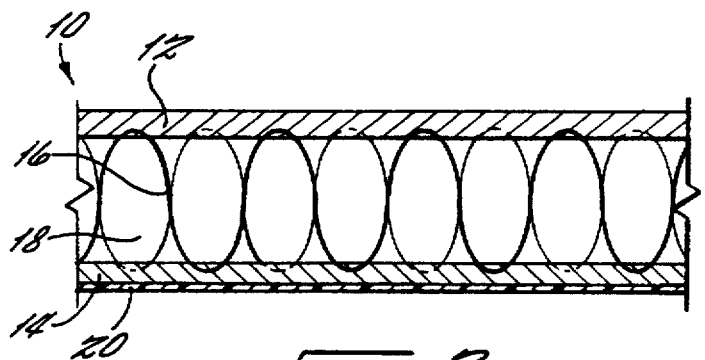
FIG. 2 is a cross-sectional schematic view of the piece of fabric shown in FIG. 1, as taken along the line 2—2.

Referring now to the drawings, FIG. 1 illustrates a piece of multi-layer fabric, shown generally at 10, according to the present invention. As illustrated in FIG. 2, which shows a cross-sectional view of the fabric of FIG. 1, the fabric 10 desirably includes a first substantially hydrophobic layer 12 and a second substantially hydrophilic layer 14. A plurality of spacer yarns 16 are secured within each of the respective knit fabric layers 12, 14, to maintain the respective layers in a spaced relationship relative to each other. The spacer yarns 16 are adapted to transfer any moisture which may come into contact with the substantially hydrophobic layer 12 to the hydrophilic layer 14. In this way, articles made from the fabric 10 of the invention, such as an item of bed clothing or the like, can absorb moisture and transfer it away from the hydrophobic surface 12 to the hydrophilic surface 14, so that the bed user is contacted by a dry-feeling surface (i.e. the hydrophobic layer.) As a result, comfort to the bed user can be enhanced. In addition, due to the weft knit structure, the fabric tends to be flexible and soft, thereby adding to user comfort.

In a preferred form of the invention, the yarns forming the first knit layer 12, i.e. the substantially hydrophobic layer, are synthetic yarns such as those made from polyester, nylon, polypropylene, blends thereof, or the like. The yarns are desirably 50–300 denier mono- or multi-filament polyester yarns, 18s–36s spun polyester yarns, or blends or combinations thereof. Particularly preferred are spun yarns or combinations of spun and filament yarns, as the spun yarns give a desirable hand and dry feel to the multi-layer fabric. This is particularly desirable because the outer surface of the hydrophobic layer 12 is intended to be the wearer-contacting surface of the multi-layer fabric 10. It is noted, however, that the spun yarns may tend to transfer moisture less readily than filament yarns; therefore, the relative amount of spun yarn used will depend on factors such as the yarn twist, tendency to hold onto moisture, and degree of moisture transport desired, among other factors. The yarns can also be textured or non-textured, though non-textured yarns are preferred due to their greater degree of moisture transport. The hydrophobic layer 12 can be of any conventional weft knit structure; particularly preferred is a knit and welt or simple jersey knit structure.

The second fabric layer 14, i.e. the substantially hydrophilic layer, is desirably knit from a natural yarn such as those made from cotton, rayon, or blends thereof. Particularly preferred are bleached, 6s–24s cotton yarns, and particularly 8s–c18s cotton yarns, due to their high degree of absorption. The size of the yarns forming the hydrophilic layer 14 can be varied, depending on the intended use of the fabric and the balance desired between moisture absorptiveness and dryability. For example, if the fabric 10 is to be used to form an item of hospital bed sheeting, the amount of hydrophilic yarns used relative to the total yarns used in the fabric should be selected based on the degree of absorption desired and the desired rapidness of drying, since as a general rule, the greater the amount of hydrophilic material, the longer the drying time required for the fabric. The hydrophilic layer 14 can be of any conventional weft knit construction; preferred are simple jersey, knit and tuck, and knit and welt structures. Particularly preferred for the hydrophilic layer 14 is a knit and welt construction, as the float yarns tend to increase the overall absorptiveness of the fabric 10.

The spacer yarns 16 are made from materials capable of wicking moisture from the hydrophobic layer 12 to the hydrophilic layer 14. Further, the spacer yarns 16 desirably are sufficiently rigid to maintain other, and to provide a degree of cushioning to the fabric 10. Preferred are non-textured polyester yarns approximately 20–300 denier in size, and particularly 70–150 denier, as these have been found to readily transport moisture from the hydrophobic layer 12 to the hydrophilic layer 14. Other yarns can be used, however, such as spun yarns or textured yarns, provided the yarns are capable of transferring moisture from the hydrophobic layer to the hydrophilic layer. Further, where filament yarns are used, the yarns can be either mono- or multi-filament yarns. Monofilament or multi-filament yarns made from a smaller number of filaments rather than a larger number of filaments are preferred, as the smaller number of filaments leaves fewer spaces between the filaments which could tend to trap moisture and thus reduce the efficiency of moisture transport. Thirty-seven filament, 100 denier yarns have been found to perform desirably in the invention, as well as 70 denier monofilament yarns.

The spacer yarns 16 desirably maintain the fabric layers in spaced relation so that air pockets 18 are formed therebetween. The air pockets 18 assist in the drying of the hydrophilic layer, as well as provide cushioning comfort to an article made from the fabric 10.

In a preferred form of the invention, the spacer yarns 16 are a single stitch in length, such that the first and second fabric layers 12, 14 are separated from each other by a single knit stitch length. Also in a preferred form of the invention, the spacer yarns 16 are of a consistent length throughout the length and width of the fabric 10, so that the fabric layers 12, 14 are maintained at a substantially consistent distance from each other across their respective dimensions. As a result, the multi-layer fabric 10 has a smooth substantially constant thickness, the dimension of which can be selected to have the optimal amount of separation for the desired end use. In a preferred form of the invention, the space between the fabric layers is about 1/16 and 3/16ths of an inch. The number of spacer yarns 16 utilized can be varied, depending on the type, stiffness, and size of yarns used, the type and size of yarns used for the first and second layers 12, 14, and the amount of cushioning and air pockets desired for the fabric 10. For example, where the spacer yarns 16 are secured to every other wale of the fabric layers 12, 14 rather than to every wale, larger denier yarns may be desirable. In a preferred form of the invention which provides a desirable amount of fabric cushioning, 100–200 denier multifilament yarns are knit onto every other needle of each of the needle beds.

The spacer yarns 16 are desirably integrally formed with the first and second layers 12, 14. For example, the spacer yarns 16 can be knit-in or laid-in (i.e. tucked in) to the knit stitches forming the first and second layers. In a preferred form of the invention, spacer yarns 16 are laid-in to each of the fabric layers 12, 14, since the laid in yarns do not plate with the fabric layer-forming yarns than those which are knit in, and as a result, less yarn is required to form the spacer yarns. Further, by laying the spacer yarns into the stitches of each of the fabric layers, the characteristics of the respective fabric layers are determined substantially entirely from the yarns from which they are knit, rather than being affected by the type of spacer yarns used. In a particularly preferred embodiment of the invention, the spacer yarns are laid into the hydrophobic layer 12 and knit into the hydrophilic layer 14, such that the spacer yarns tend to plate on the outer surface (i.e. that remote from the hydrophobic layer) of the hydrophilic layer. In this embodiment of the invention, the spacer yarns 16 tend to protect the hydrophilic yarns, which typically tend to be relatively weaker than the polyester yarns used as the spacer yarns in a preferred embodiment of the invention. Where this embodiment of the invention is knit on a cylinder and dial type circular knitting machine, the hydrophilic layer 14 is preferably knit on the cylinder needles, as superior plating tends to be achieved due to the way the yarn is tensioned in the cylinder hooks and the force of the knit fabric pulling the yarns toward the needle backs.

The fabric 10 also desirably includes a moisture resistant layer 20 secured proximate the hydrophilic layer 14, to prevent the transfer of moisture away from the hydrophilic layer. In a particularly preferred embodiment of the invention, the moisture resistant layer 20 is in the form of a plastic layer coated or otherwise secured substantially continuously across the hydrophilic layer 14. The coating process can be of any conventional fabric coating process such as extrusion, melt bonding, padding, spraying, roller coating, or the like. The plastic material can be of any conventional moisture resistant material, such as vinyl. The knit structure discussed above in which the spacer yarns 16 are knit into the hydrophilic layer 14 in order that they tend to plate on the yarns forming that layer, performs particularly well when the moisture resistant layer is in the form of a plastic layer coated onto the hydrophilic fabric layer. Because the spacer yarns 16 are plated on the outside of the hydrophilic layer 14, the coated plastic tends to bond to those yarns, thereby leaving the bulk of the hydrophilic material available to absorb moisture.

As previously stated, the sizes of the yarns forming each of the respective parts of the multi-layer fabric can be selected to give desired fabric properties and to take into account cost and availability of various yarns. One combination which the inventor has found to be desirable is a fabric having a hydrophobic layer knit from 300 denier multifilament polyester, a hydrophilic layer knit from 14s cotton yarns, and spacer yarns of 200 denier untextured polyester.

Figure 3:
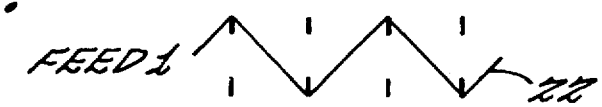
FIG. 3 shows an exemplary knitting sequence for forming a fabric according to the present invention.
Figure 3:
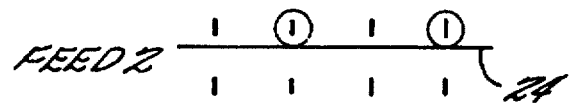
Figure 3:
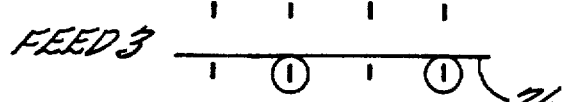
Figure 3:
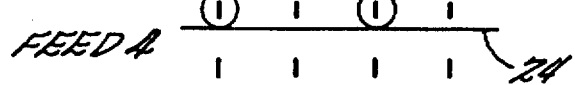
Figure 3:
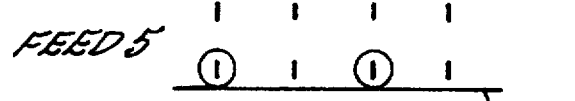

The method of producing the fabric 10 is desirably formed as follows, with reference to FIGS. 3–5. FIG. 3 illustrates an exemplary pattern repeat for forming a fabric according to the instant invention, with the needles of the knitting machine being arranged in interlock gating. Interlock gating, which is well known in the art, uses two beds of needles which are exactly opposite each other rather than being laterally offset such that only one of the opposing needles knits at a time. Two separate cam systems are provided on each needle bed to control needle selection, one controlling short needles and the other controlling long needles. Generally, the needles are arranged in beds so that they alternate between long and short needles, and the opposing needle in the other bed is the opposite type of needle from that in the first bed. Feed 1 of the sequence illustrates the yarn 22 as it is fed in a reciprocating manner between the two needle beds; this yarn 22 will form the spacer yarns 16 in the fabric 10. Feeds 2 and 4 form the first fabric layer from yarns 24, while feeds 3 and 5 form the second fabric layer from yarns 26. A knit-welt fabric structure is formed for each of the first and second fabric layers, as illustrated by the way each feed knits only on every other needle, floats over the adjacent needle, then knits on the following needle. As illustrated, the yarn 22 which forms the spacer yarns 16 is laid into every other needle on each of the two beds; thus the spacer yarns will be secured to and extend from every other wale of each of the fabric layers 12, 14.

In a preferred form of the invention, the knitting sequence illustrated would be repeated in reverse to form a ten feed repeat, in a manner which will be understood by those of ordinary skill in the art, in order to form a balanced fabric. Though variations of this sequence could be used within the scope of the invention, it is noted that in some embodiments a special hold back device (e.g. a presser) will need to be utilized. It has been discovered, however, that by knitting the feed(s) following the feed in which the yarns are laid-in (e.g., in FIG. 3, Feeds 2 and 3 follow the Feed 1 laid-in yarn) on needles adjacent to or surrounding those having the tuck loops, the yarns knit onto those succeeding feeds hold the tuck loops back when the needles holding the tuck loops are moved for knitting a subsequent feed (e.g. Feed 4 in FIG. 3). Thus, when this type of feed arrangement is utilized, the need for a supplemental hold back device can be avoided.

Figure 4:
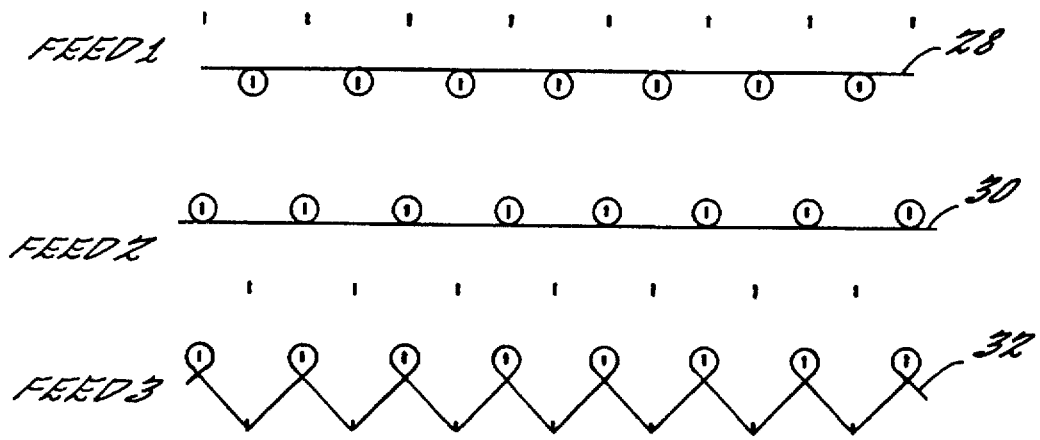
FIG. 4 is an alternative knitting sequence for forming a fabric according to the present invention.

FIG. 4 illustrates an alternate method of knitting a fabric 10 according to the invention, with the needles being arranged in a standard or rib gating. As illustrated, the needles in the opposite beds are laterally offset from each other. As illustrated at Feed 1, yarn 28 is knit onto every needle of the bed to form a first fabric layer and yarn 30 is knit on every needle of the other needle bed at Feed 2. The yarn 32 is then knit in a reciprocating manner on each needle of each of the respective first and second needle beds at Feed 3, such that it is knit on the needles of one needle bed and laid into the needles of the opposite needle bed. In this way, to form the spacer yarns 16 which secure the two layers 12, 14 together in a spaced relationship relative to each other are formed such that the spacer yarns do not plate on the layer 12, 14 in which the loops were knitted in, and not to plate on the opposite fabric layer where the yarn was laid-in rather than knit-in.

Figure 5:
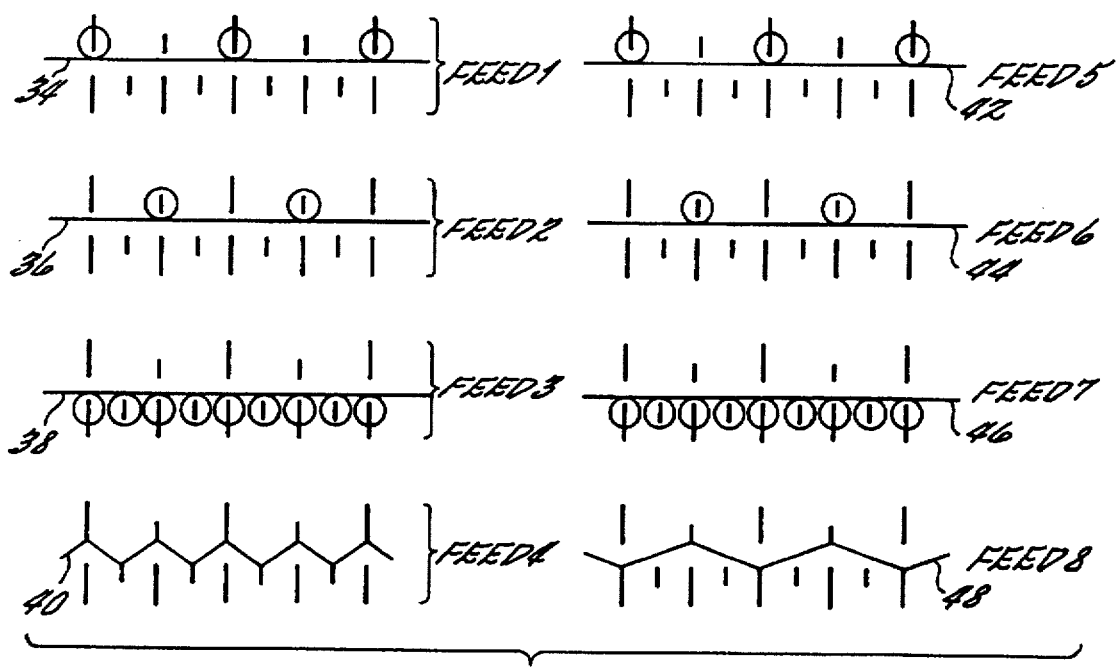
FIG. 5 is a further alternative knitting sequence for forming a fabric according to the present invention.

FIG. 5 illustrates a somewhat different method of knitting the fabric be, again using an interlock needle gating rather than a standard gating such as that shown in FIG. 4. In addition, the machine is arranged such that the upper needle bed has half the needles as the lower needle bed. The yarn 34 is knit on the long needles only at Feed 1 while yarn 36 is knit on the short needles only of the same needle bed at Feed 2. The yarn 38 is then knit onto every needle of the opposing needle bed at Feed 3. The yarn 40 at Feed 4 reciprocates between the two needle beds, where it forms a tuck loop at each of the short needles only, to form some of the spacer yarns 16 in the finished fabric. Feeds 5, 6, and 7 are then knit in the same manner as Feeds 1-3 with the yarns 42, 44, 46, respectively, and Feed 8 is then knit such that yarn 48 knits on every short needle of the top bed and every other long needle on the bottom bed.

The specific examples described are for illustrative purposes only. It is noted that various knit pattern combinations can be used within the scope of the invention. For example, the spacer yarn could be inlaid on two or more needles, then the next two needles could be skipped, etc. As discussed previously, the spacer yarns can be knit into one fabric layer, and laid into the other. Similarly, two different knit structures (simple jersey, knit and welt, etc.) can be used for the two fabric layers, or the structures can be the same.

In the drawings and the specification, there has been set forth preferred embodiments of the invention and, although specific terms are employed, the terms are used in a generic and descriptive sense only and not for the purpose of limitation, the scope of the invention being set forth in the following claims.

That which is claimed is:

1. A method of making a weft knit, wicking fabric on a dual bed knitting machine comprising the steps of:

knitting a first discrete fabric layer from a hydrophobic yarn on a first needle bed of the weft knitting machine, knitting a second discrete fabric layer from a hydrophilic yarn on a second needle bed of the weft knitting machine, and knitting a series of courses reciprocating between the first and second needle beds to form a plurality of spacer yarns the spacer yarns securing the first and second fabric layers together in a spaced relationship separated from each other, said series of courses being knit from a moisture transporting yarn for wicking moisture from the first fabric layer to the second fabric layer.

2. The method according to claim 1, wherein said step of knitting a series of courses reciprocating between the first and second needle beds to form a plurality of spacer yarns securing the first and second fabric layers together in a spaced relationship to each other is performed such that the first and second fabric layers are substantially consistently spaced from each other across their respective widths.

3. The method according to claim 1, wherein said step of knitting a series of courses reciprocating between the first and second needle beds to form a plurality of spacer yarns securing the first and second fabric layers together in a spaced relationship to each other is performed such that each course of said series of courses forming the plurality of spacer yarns reciprocates directly from one needle bed to the other needle bed so that the spacer yarns extend substantially vertically between the first and second fabric layers.

4. The method according to claim 1, wherein said step of knitting first and second fabric layers and said series of courses reciprocating between the first and second needle beds further comprising knitting said second discrete fabric layer on a dial needle bed of a circular knitting machine having cylinder and dial needle beds.

5. The method according to claim 1, wherein said step of knitting a series of courses reciprocating between the first and second needle beds comprises laying the yarn into the first fabric layer.

6. The method according to claim 5, wherein said step of knitting a series of courses reciprocating between the first and second needle beds comprises laying the yarn into the second fabric layer.

7. The method according to claim 5, wherein said step of knitting a series of courses reciprocating between the first and second needle beds comprises knitting the yarn into the second fabric layer.

8. The method according to claim 1, further comprising the step of coating a surface of the hydrophilic layer remote from the hydrophobic layer with a layer of substantially continuous plastic, to thereby provide a moisture resistant surface on the fabric.

9. A multi-layer weft knit fabric for wicking moisture away from a first surface comprising:

a first substantially hydrophobic weft knit discrete fabric layer, a second substantially hydrophilic weft knit discrete fabric layer, and a plurality of moisture transporting spacer yarns secured within the knit structure of each of said first and second layers and extending between the layers to secure the layers in spaced relationship separated from each other, said spacer yarns promoting wicking of moisture from said first knit substantially hydrophobic fabric layer to said second substantially hydrophilic layer.

10. The fabric according to claim 9, further comprising a moisture-resistant layer secured adjacent said hydrophilic layer.

11. The fabric according to claim 10, wherein said moisture-resistant layer comprises a plastic coating on a surface of said hydrophilic layer remote from said hydrophobic layer.

12. The fabric according to claim 11, wherein said plastic coating comprises vinyl.

13. The fabric according to claim 9, wherein spacer yarns are laid into knit stitches forming said hydrophobic layer.

14. The fabric according to claim 13, wherein spacer yarns are laid into knit stitches forming said hydrophilic layer.

15. The fabric according to claim 14, wherein spacer yarns are knit into knit stitches forming said hydrophilic layer.

16. The fabric according to claim 9, wherein said hydrophobic layer comprises a polyester yarn.

17. The fabric according to claim 16, wherein said hydrophobic layer comprises a polyester monofilament yarn about 70 denier in size or smaller.

18. The fabric according to claim 16, wherein said hydrophobic layer comprises a multifilament polyester yarn about 50–300 denier in size.

19. The fabric according to claim 16, wherein said hydrophobic layer comprises a spun 18s–36s polyester yarn.

20. The fabric according to claim 9, wherein said spacer yarns comprise non-textured synthetic yarns.

21. The fabric according to claim 9, wherein said hydrophilic layer comprises a yarn selected from the group consisting of cotton, rayon, and blends thereof.

22. The fabric according to claim 9, wherein said spacer yarns are knit into knit stitches forming said hydrophilic layer, and further comprising a moisture-resistant coating on a surface of said hydrophilic layer remote from said hydrophobic layer.

23. A multi-layer, weft knit fabric comprising:
   a first discrete layer knit from a hydrophobic yarn,
   a second discrete layer knit from a hydrophilic yarn,
   a plurality of moisture transporting spacer yarns extending substantially between the first and second layers to hold them in a spaced relationship to each other and for wicking moisture from the first layer to the second layer, and
   a moisture-resistant layer secured adjacent the second layer, to block the transfer of moisture from the second layer.

24. The fabric according to claim 23, wherein said first layer comprises a spun polyester yarn.

25. The fabric according to claim 24, wherein said spacer yarns comprise non-textured polyester yarns.

26. The fabric according to claim 23, wherein said first layer comprises a spun polyester yarn, said second layer comprises a natural fiber yarn, and said spacer yarns comprise a non-textured polyester yarn.

27. The fabric according to claim 23, wherein said spacer yarns are laid into said first fabric layer and knit into said second fabric layer in a plated relationship with the hydrophilic yarn, and
   said moisture-resistant layer comprises a plastic coating secured to a surface of said second fabric layer remote from said first fabric layer.

28. An item of bedclothing for incontinent use comprising:
   an upper substantially hydrophobic weft knit discrete fabric layer,
   a lower substantially hydrophilic weft knit discrete fabric layer, and
   a plurality of moisture transporting spacer yarns secured within the knit structure of each of the upper and lower layers and extending between the layers to secure them in spaced relationship separated from each other, said spacer yarns for wicking moisture from the upper substantially hydrophobic fabric layer to the lower substantially hydrophilic layer.

29. The bedclothing according to claim 28, further comprising a moisture-resistant layer secured adjacent said hydrophilic layer.

30. The bedclothing according to claim 28, wherein said moisture-resistant layer comprises a plastic coating on a surface of said hydrophilic layer remote from said hydrophobic layer.

31. The bedclothing according to claim 30, wherein spacer yarns are laid into knit stitches forming said hydrophobic layer, and knit into knit stitches forming said hydrophilic layer.

* * * * *